(12) United States Patent
Bryselbout

(10) Patent No.: US 7,223,607 B2
(45) Date of Patent: May 29, 2007

(54) PROCESS AND DEVICE FOR THE DETECTION OF HYDROCARBONS IN A GAS

(75) Inventor: Francis Bryselbout, Le Mesnil St Denis (FR)

(73) Assignee: L'Air Liquide Societe Anonyme pour l'Etude et l'Exploitation des Procedes Georges Claude, Paris (FR)

( * ) Notice: Subject to any disclaimer, the term of this patent is extended or adjusted under 35 U.S.C. 154(b) by 815 days.

(21) Appl. No.: 10/062,546

(22) Filed: Feb. 5, 2002

(65) Prior Publication Data

US 2002/0104368 A1    Aug. 8, 2002

(30) Foreign Application Priority Data

Feb. 6, 2001    (FR)    ................................. 01 01596

(51) Int. Cl.
G01N 33/00    (2006.01)
G01N 25/18    (2006.01)
G01N 27/00    (2006.01)
G01N 25/22    (2006.01)
G01N 25/26    (2006.01)

(52) U.S. Cl. .................... 436/139; 422/50; 422/83; 422/94; 422/98; 73/1.01; 73/1.02; 73/23.2; 73/23.31; 436/149; 436/151; 436/152; 436/154; 436/155; 436/158; 436/159; 436/160; 436/143; 436/144

(58) Field of Classification Search ............... 422/83, 422/94, 98; 73/1.01, 1.02, 23.2, 23.31; 436/149, 436/151, 152, 154, 155, 158, 159, 160, 139, 436/143, 144
See application file for complete search history.

(56) References Cited

U.S. PATENT DOCUMENTS 3,753,656 A * 8/1973 Matson et al. ............. 436/39
3,762,878 A 10/1973 Villalobos
4,042,332 A 8/1977 Saitoh et al.
4,102,648 A * 7/1978 Hartmann et al. ............. 422/54
4,302,422 A * 11/1981 Takahashi ..................... 422/88
4,934,147 A * 6/1990 Eyre ........................... 62/656

(Continued)

FOREIGN PATENT DOCUMENTS

DE    198 49 105 C1    9/2000

(Continued)

OTHER PUBLICATIONS

Search Report issued in French Application No. 598958, dated Nov. 8, 2001.

*Primary Examiner*—Brian Sines
(74) *Attorney, Agent, or Firm*—Buchanan Ingersoll & Rooney PC

(57) ABSTRACT

The invention relates to a process for the detection of hydrocarbons other than methane in a gas predominantly or essentially comprising oxygen, as well as methane and the said hydrocarbons other than methane, the said process comprising:
- a stage of detection of the combined hydrocarbons in the said gas, providing a first value for the combined hydrocarbons,
- a stage of combustion of the hydrocarbons other than methane,
- a stage of detection of methane in the said gas, providing a second value,
- a stage of calculation of the amount of hydrocarbons other than methane by the difference between the first value and the second value.

The invention also relates to a device for implementing this process.

24 Claims, 7 Drawing Sheets

U.S. PATENT DOCUMENTS 5,073,753 A * 12/1991 Collings et al. ............ 324/468
5,425,240 A *  6/1995 Jain et al. ...................... 62/641
5,595,709 A *  1/1997 Klemp ........................ 422/88
5,629,208 A *  5/1997 Darredeau et al. ............ 436/55
5,765,397 A *  6/1998 Honda et al. ................. 62/646

FOREIGN PATENT DOCUMENTS

| | | | |
|---|---|---|---|
| EP | 0 848 250 A2 | 6/1998 |
| FR | 2 237 193 | 7/1975 |
| JP | 56-4052 A | 1/1981 |
| JP | 56-16870 A | 2/1981 |
| JP | 10-253594 A | 9/1998 |

* cited by examiner

PROCESS AND DEVICE FOR THE DETECTION OF HYDROCARBONS IN A GAS

BACKGROUND OF THE INVENTION

1. Field of the Invention

The invention relates to the field of the detection of hydrocarbons other than methane in a gas comprising or essentially comprising oxygen and in particular a gas comprising at least 95% of oxygen with impurities, in particular hydrocarbon impurities, the said hydrocarbon impurities being, for example, present at less than 200 ppm.

The invention also relates to units for the production of gases from the air. This is because the presence of non-methane hydrocarbons in the liquid oxygen bath of the evaporators of these production units leads to a risk of explosion when certain concentration limits are exceeded. These limits are defined in the operating instructions for the production units.

2. Description of the Related Art

The techniques currently used to identify and detect these hydrocarbons are, on the one hand, chromatography and, on the other hand, infrared spectrometry (FTIR).

Chromatography is a technique which has been used for a very long time. It is sequential and only allows the detection and measurement of a few preselected hydrocarbons. The capital investment and the maintenance costs of the chromatograph are high.

Infrared spectrometry (FTIR) is a technique which, although more effective than chromatography, is not completely comprehensive, as it requires an examination of the spectrum in order to search for an impurity which would not have been preselected. In addition, the equipment requires a high capital investment.

The problem is thus posed of finding a novel method and a novel device which make possible continuous measurement and continuous detection of hydrocarbons other than methane in a gas essentially comprising oxygen.

The problem is also posed of finding a method and a device which are simpler to employ and less costly than the prior techniques and devices.

The problem is also posed of finding a method and a device which make possible continuous measurement and continuous detection of hydrocarbons other than methane in a gas essentially comprising oxygen, the said hydrocarbons other than methane being present, with respect to methane, in a proportion of the order of a few percent.

The problem is also posed of ensuring the safety of units for the production of gases from the air, comprising an evaporator, by the continuous comprehensive detection of nonmethane gaseous hydro-carbons at a concentration of a few ppm (for example: less than 5 ppm) in the oxygen of the evaporator, which can itself comprise methane, for example at approximately 50 ppm.

SUMMARY OF THE INVENTION

A subject-matter of the invention is first of all a process for the detection of hydrocarbons other than methane in oxygen or in a gas comprising or essentially comprising oxygen (the oxygen additionally being mixed with methane and the said hydrocarbons other than methane), the said process comprising:

a stage of detection of the combined hydrocarbons in the said oxygen or in the said gas, providing a first value for the combined hydrocarbons, a stage of combustion of the hydrocarbons other than methane, a stage of detection of methane in the said oxygen or in the said gas, providing a second value, preferably followed by, a stage of calculation of the amount of hydrocarbons other than methane by the difference between the first value and the second value.

Such a process makes it possible to carry out a continuous measurement of the hydrocarbons other than methane.

The stages of detection can be carried out by a flame ionization detector. A detection system is thus produced which is simple to use, which operates continuously, which is accurate, which is less expensive and which requires less maintenance than the known systems.

According to one embodiment, the hydrocarbons other than methane are incinerated in a catalyst.

In addition, hydrogen can be mixed with the gas to be analysed, so that the mixture exhibits an $H_2:O_2$ ratio close to or of the same order as the $H_2:O_2$ ratio in the air.

The temperature of the catalyst is preferably such that less than 5% of the methane present in the gas is incinerated.

The invention also relates to a process for the detection of hydrocarbons other than methane in a liquid oxygen bath of an evaporator of a unit for the production of gases from the air, comprising:

a withdrawal of a sample of liquid oxygen from the said bath, an evaporation of the said liquid oxygen, producing an evaporated gas, a process for the detection of hydrocarbons other than methane in the said evaporated gas, as described above.

The withdrawal of the sample is preferably carried out using a pipe of a pump for raising liquid or over a sampler of lift type, which makes it possible to sample the gas rapidly and thus to analyse at each instant a fairly representative sample of the mixture to be analysed at the same instant.

The invention also relates to a device for the detection of hydrocarbons other than methane in a gas predominantly or essentially comprising oxygen, as well as methane and the said hydrocarbons other than methane, which is especially suitable for the implementation of a process as described above, the said device comprising:

means for the detection of the combined hydrocarbons in the said gas, providing a first value for the combined hydrocarbons, means for the combustion of the hydrocarbons other than methane, means for the detection of methane, and preferably, means for, or especially programmed for, the calculation of the amount of hydrocarbons other than methane by the difference between the first value and the second value.

The invention also relates to a device for the detection of hydrocarbons other than methane in a liquid oxygen bath of an evaporator of a unit for the manufacture of gases from the air, comprising:

means for the withdrawal of a sample of liquid oxygen from the said bath, means for the evaporation of the said liquid oxygen, producing an evaporated gas, a detection device as described above.

Means can additionally be provided for triggering an alarm when the concentration or the level of hydrocarbons other than methane in the said evaporated gas exceeds a certain limit value.

BRIEF DESCRIPTION OF THE FIGURES OF THE DRAWING

The characteristics and advantages of the invention will become more clearly apparent in the light of the description which will follow. This description relates to implementational examples, given by way of explanation and without implied limitation, with reference to appended drawings, in which.

DETAILED DESCRIPTION OF THE PREFERRED EMBODIMENTS OF THE INVENTION

Figure 1:
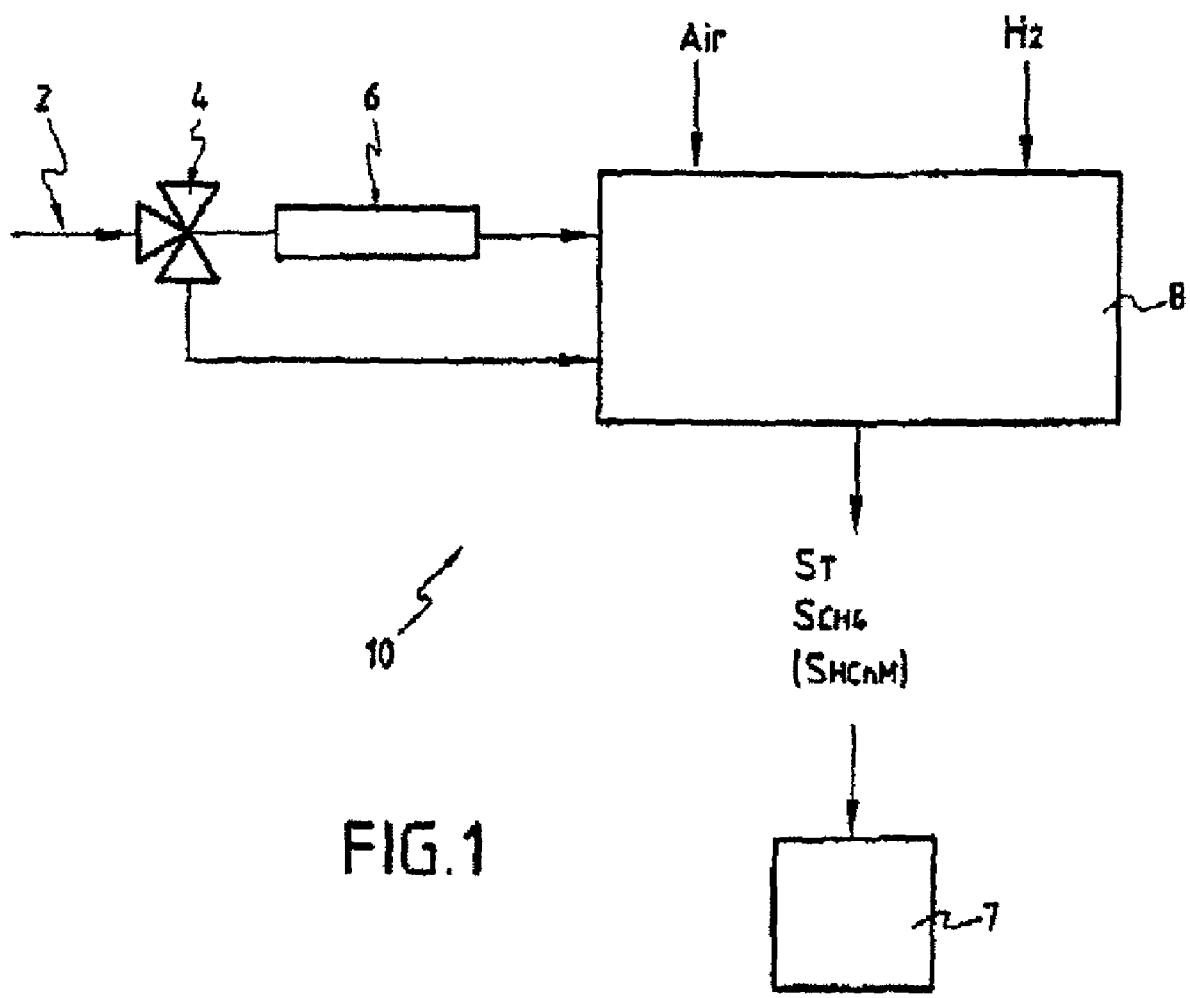
FIG. 1 represents an implementational example of the invention.

An implementational example of the invention is given in FIG. 1.

In this figure, reference 2 denotes an inlet of a gas to be measured which is composed of or which comprises oxygen or essentially oxygen and which includes hydrocarbon impurities, for example at less than approximately 200 ppm, for example 100 ppm or 50 ppm or at a level of the order of a few tens of ppm.

The hydrocarbon impurities may include, on the one hand, methane and, on the other hand, nonmethane gaseous hydrocarbons. According to one example, methane is present at a level of approximately 50 ppm and the non-methane gaseous hydrocarbons are present at a level of the order of 5 ppm.

Other impurities can additionally be present, in particular nitrogen or argon, but the gas essentially comprises oxygen at least 95%, preferably at least 99% or 99.5%.

In the case where only hydrocarbons are present, at a level of 200 ppm, the gas comprises 99.98% of oxygen.

Reference 10 denotes a system for analysis according to the invention.

The gas to be measured can, via a valve 4, either be conveyed over a catalyst 6, which makes it possible to incinerate the nonmethane gaseous hydro-carbons (HCnM, or measurement in $CH_4$ mode), and then over a detector 8, or be conveyed directly over the detector 8. In the second case, all the hydrocarbons are detected (total hydrocarbons, or HCT, or measurement in HCT mode) and the detector emits a signal ST representative of the total amount of hydrocarbons. In the first case, only methane arrives at the detector and the latter emits a signal S4 representative of the total amount of methane. Processing of the signals, for example using numeric means for signal processing and for calculation 7, subsequently makes it possible, by ST–S4 subtraction, to deduce a measurement for the combined nonmethane gaseous hydrocarbons.

A catalyst which can be used for the combustion of the nonmethane gaseous hydrocarbons can be:

- a metal oxide or a mixture of metal oxides which are deposited on an absorbent of zeolite type (alumina or other type, and the like). The metal oxide can be: $MnO_2$ (manganese oxide), CuO and $Cu_2O$ (copper oxide), $ZrO_2$ (zirconium oxide), and the like.
- a precious metal or a mixture of precious metals which are deposited on an adsorbent of zeolite type (alumina or other type, and the like). The metal can be, for example: Pt (platinum) or Ni (nickel) or Rh (rhodium).

Use may also be made of Pt or Ni gauze, sponge or wire. Another example of a catalyst is carulite, with the composition: 60% to 75% of $MnO_2$, from 11% to 14% of CuO, and from 15% to 16% of $Al_2O_3$. Yet another example of a catalyst is hopcalite, with the composition 33–44% $MnO_2$ and 22–36% CuO (the remainder being a binder).

The detector 8 is, for example, a flame ionization detector. In this case, hydrogen is additionally mixed with the gas to be analysed at the inlet of the detector 8. Air is injected above the flame of hydrogen and of gas to be analysed, this air serving to remove the water vapour formed by the combustion.

An example of such a detector is that sold by Environnement S.A. (111, Bd Robespierre, 78300 POISSY, FRANCE) under the reference HC51M.

The hydrogen flow rate is preferably such that the composition of the hydrogen-gas to be analysed (oxygen) mixture is between 10% and 40% or is close to or is of the order of the $O_2$-$H_2$ ratio in the air (approximately 30%). This makes it possible for the detector to be able to operate with an oxygen sample flow rate while obtaining the same detection sensitivity as for tests carried out on air.

An increase in the hydrogen flow rate doubtless also has the effect of modifying the shape of the flame where the ionic current produced by the combustion of the HCnMs is collected. The collecting electrode for this current is positioned above the flame and the proportion of ions collected may be different according to the shape of the flame.

By way of example, the hydrogen flow rate is approximately 130 ml/min (in contrast to 40 ml/min for use in air), the sample (oxygen) and air (bleed or removal of the water vapour) flow rates being 80 ml/min and 400 ml/min respectively.

The temperature of the catalyst 6 is preferably chosen such that as little as possible of $CH_4$ is incinerated. This is because, in the case of carulite, for a temperature of approximately 210° C., it could be observed that a not insignificant proportion of $CH_4$ was incinerated. In point of fact, the calculation of the concentration of the HCnMs consists in knowing the difference between the measurement in HCT mode (when the sample passes directly into the detector) and the measurement in $CH_4$ mode (when the sample passes into the catalyst before going into the detector). The concentration of HCnM is then significantly increased.

In order to reduce the combustion of methane in the catalyst, the temperature was adjusted in two stages (case of carulite):

1. Regulation of the temperature at 163° C. The analysis of a mixture comprising 10 ppm of $CH_4$+1 ppm of $C_2H_6$ in oxygen functions well but the analysis of a mixture comprising 52.2 ppm of $C_2H_6$+52.5 ppm of $CH_4$ in oxygen shows that approximately 10% of $C_2H_6$ is not incinerated, a proportion which cannot be evaluated with accuracy over a $C_2H_6$ content of 1 ppm.

2. Regulation of the temperature at 182° C. The results are satisfactory with regard to the 2 preceding mixtures and with regard to a mixture which does not comprise $CH_4$ but only 8 ppm of $C_2H_6$ in oxygen, for which all the $C_2H_6$ is incinerated.

The regulation of the operating temperature of the converter for nonmethane hydrocarbons, for example between 160° C. and 190° C., thus makes it possible not to lose methane (or to lose at most a few % thereof, for example at most 3% or 5%) while converting the nonmethane hydrocarbons (HCnMs) of the sample of oxygen to be analysed.

Figure 2:
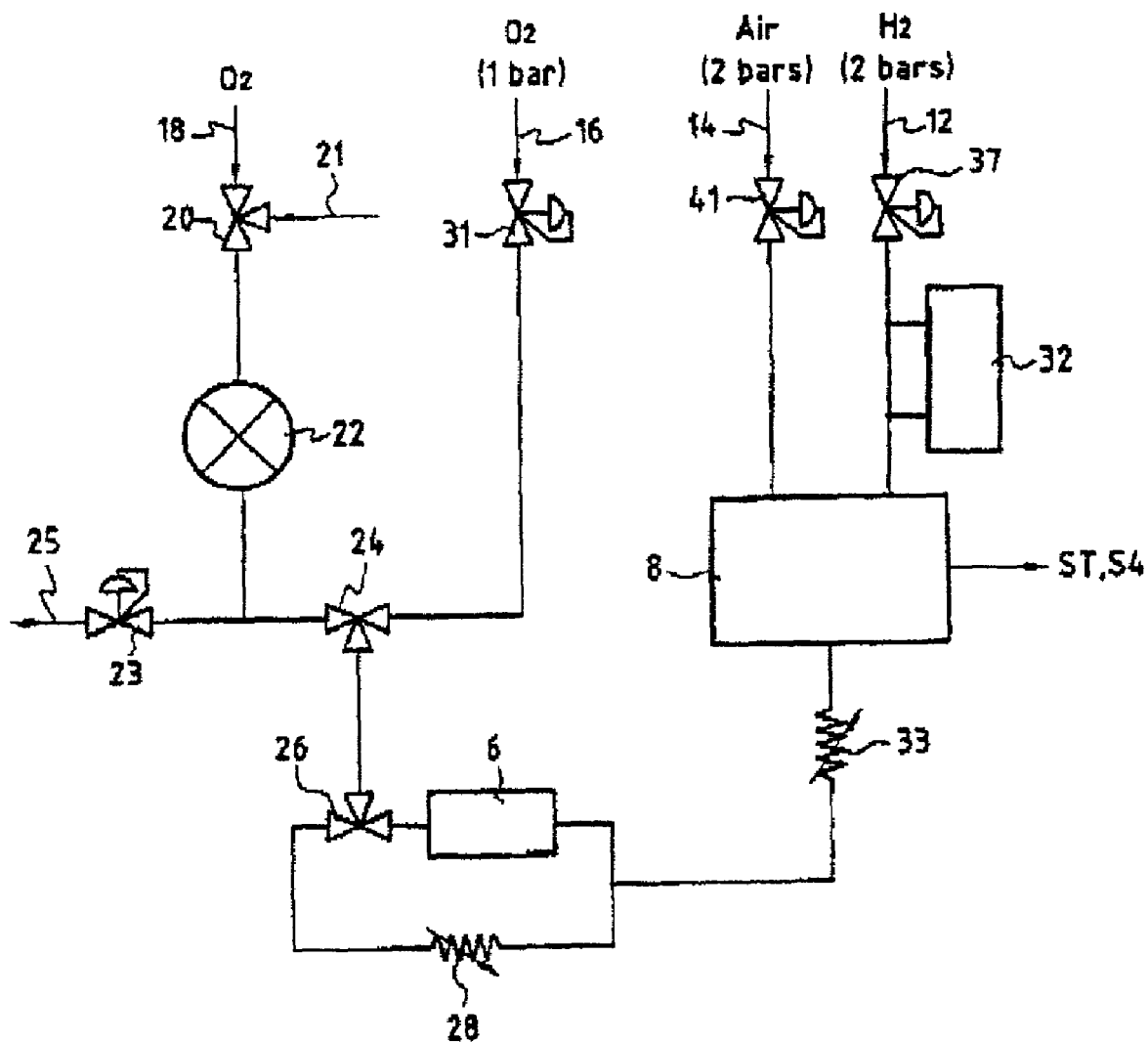
FIG. 2 represents the structure of a detector which can be used in the context of the present invention.

FIG. 2 represents a detailed example of the detection system 10 with a detector, of HC51M type already mentioned above, as used in the context of the present invention. This system employs a flame ionization detector 8.

As already explained above, hydrogen and air are introduced into this detector via routes 12 and 14 respectively.

Oxygen, at a pressure of approximately one bar, is introduced via route 16, in order to zero the device.

The oxygen to be analysed is introduced via route 18, route 21 making possible the introduction of a standard gas at atmospheric pressure.

Route 25 makes it possible to bleed off an excess of samples introduced into the circuit.

In a more detailed way, route 12 successively comprises a regulator 37, at the terminals of which is positioned an ignition loop 32.

Route 14 successively comprises a purifier (not represented) and a regulator 41.

Route 16 comprises a purifier (not represented) and a regulator 31 and is connected to a three-way electrically operated valve 24.

The sample of gas to be analysed, a valve 20 and a pump 22 also arrive via this electrically operated valve 24. An excess of sample is bled off via a regulator 23.

A three-way valve 26 makes it possible to convey a gas to be analysed either directly to the analyser 30 (the reference 28 denotes a charge-balancing capillary) or to a catalyst 6 in order to incinerate the nonmethane hydrocarbons. The reference 33 denotes a variable capillary which makes it possible to regulate the flow rate at the inlet of the detector 30. The latter delivers signals ST and S4, from which a calculator can calculate, by subtraction, a signal representative of the amount of nonmethane hydrocarbons.

Figure 3:
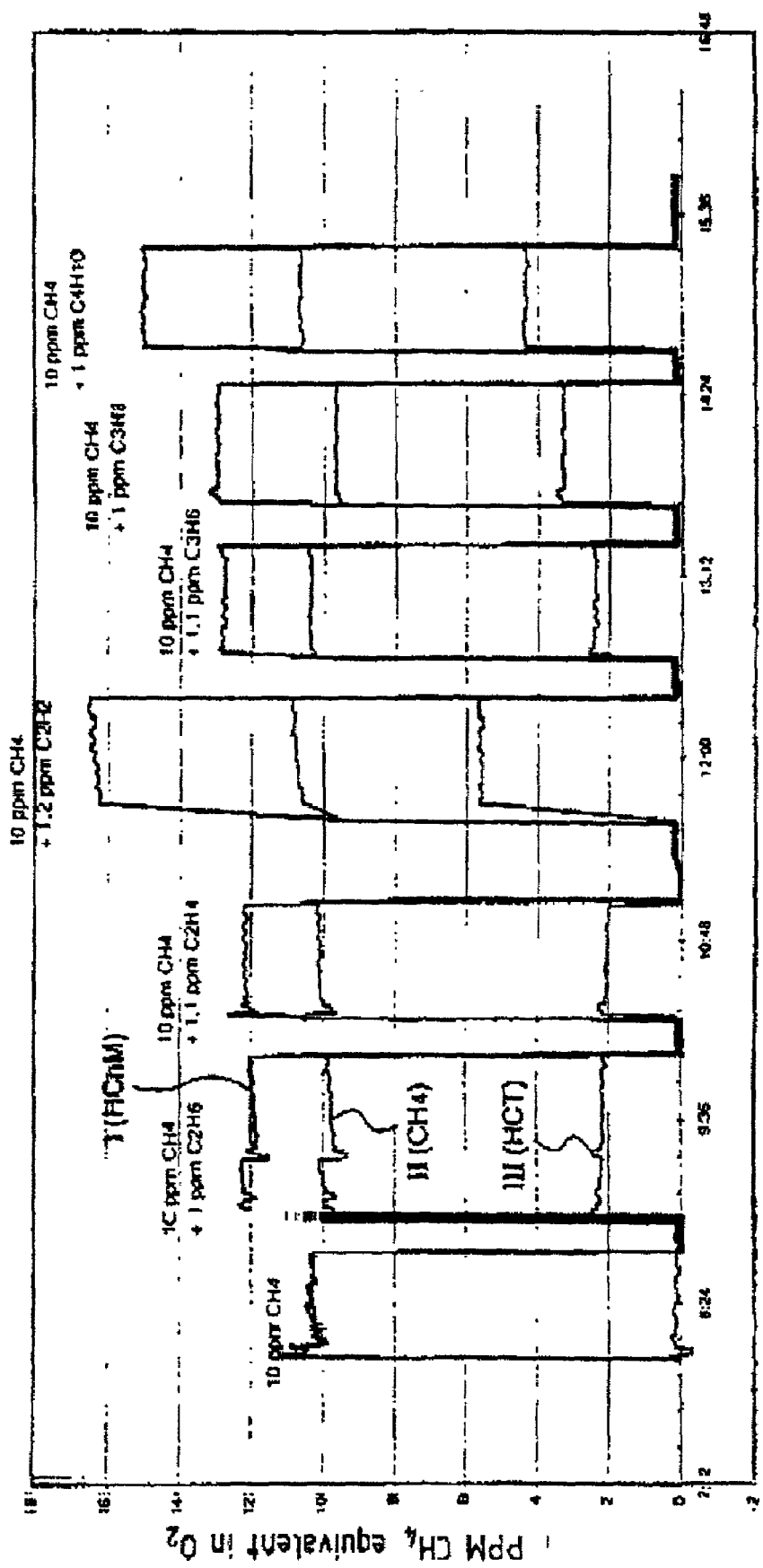
FIG. 3 represents a test of response of nonmethane hydrocarbons in oxygen.

FIG. 3 represents a test of response of $C_n$ (n=2, 3 or 4) nonmethane hydrocarbons (HCnMs) in oxygen in the presence of 10 ppm of $CH_4$. The trials relate to:

10 ppm of $CH_4$ in $O_2$
10 ppm of $CH_4$+1 ppm of $C_2H_6$ in $O_2$
10 ppm of $CH_4$+1.1 ppm of $C_2H_4$ in $O_2$
10 ppm of $CH_4$+1.2 ppm of $C_2H_2$ in $O_2$
10 ppm of $CH_4$+1.1 ppm of $C_3H_6$ in $O_2$
10 ppm of $CH_4$+1.1 ppm of $C_3H_8$ in $O_2$
10 ppm of $CH_4$+1 ppm of $C_4H_{10}$ in $O_2$ The device used is of the type sold by Environnement S.A. (111, Bd Robespierre, 78300 POISSY, FRANCE) under the reference HC51M, with the following operating conditions:

catalyst temperature: 182° C.,
hydrogen flow rate: approximately 130 ml/min,
sample flow rate: 80 ml/min,
oxidant air flow rate: 400 ml/min,
catalyst: carulite (composition indicated above).

Curve I gives the amount of HCnM, curve II gives the amount of $CH_4$ and curve III gives the total amount of hydrocarbons.

These trials indicate that the response of the flame ionization detector is indeed proportional to the number of carbon atoms in the $C_nH_m$ to be measured, except for $C_2H_2$ ($C_2H_2$ has a better response). The device is capable of detecting less than 1 ppm of $C_nH_m$ as $CH_4$ equivalent in oxygen comprising 10 ppm of $CH_4$. That is, less than 0.5 ppm of $C_2$, less than 0.3 ppm of $C_3$ and less than 0.25 ppm of $C_4$.

This test gives similar or identical results for sensitivity to a test carried out for measurements of CnHm in air (but with different conditions: catalyst temperature of 210° C., hydrogen flow rate of 40 ml/min, sample flow rate of 80 ml/min, oxidant air flow rate of 400 ml/min).

In FIGS. 4A to 6B, curve I represents the change in the concentration of HCnM, as $CH_4$ equivalent, and curve II represents the change in the concentration of HCT, also measured as $CH_4$ equivalent.

Figure 4A:
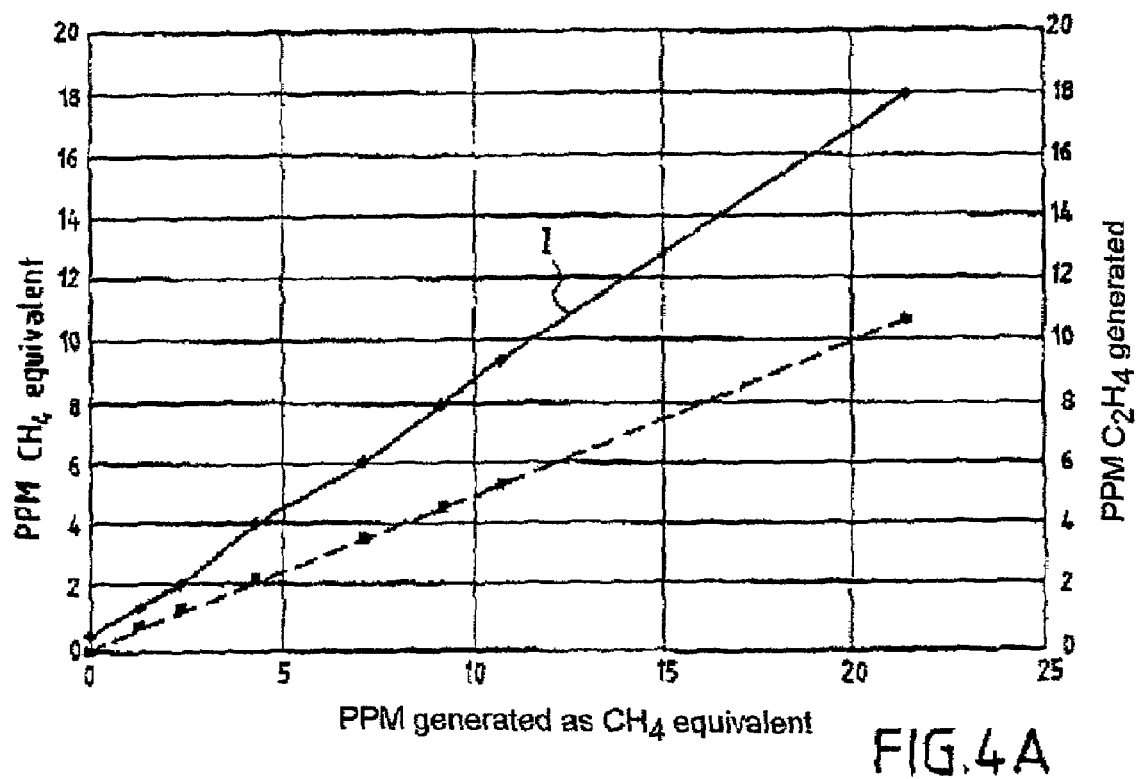
FIGS. 4A to 6B represent various trials carried out on mixtures of oxygen and of hydrocarbon.
Figure 4B:
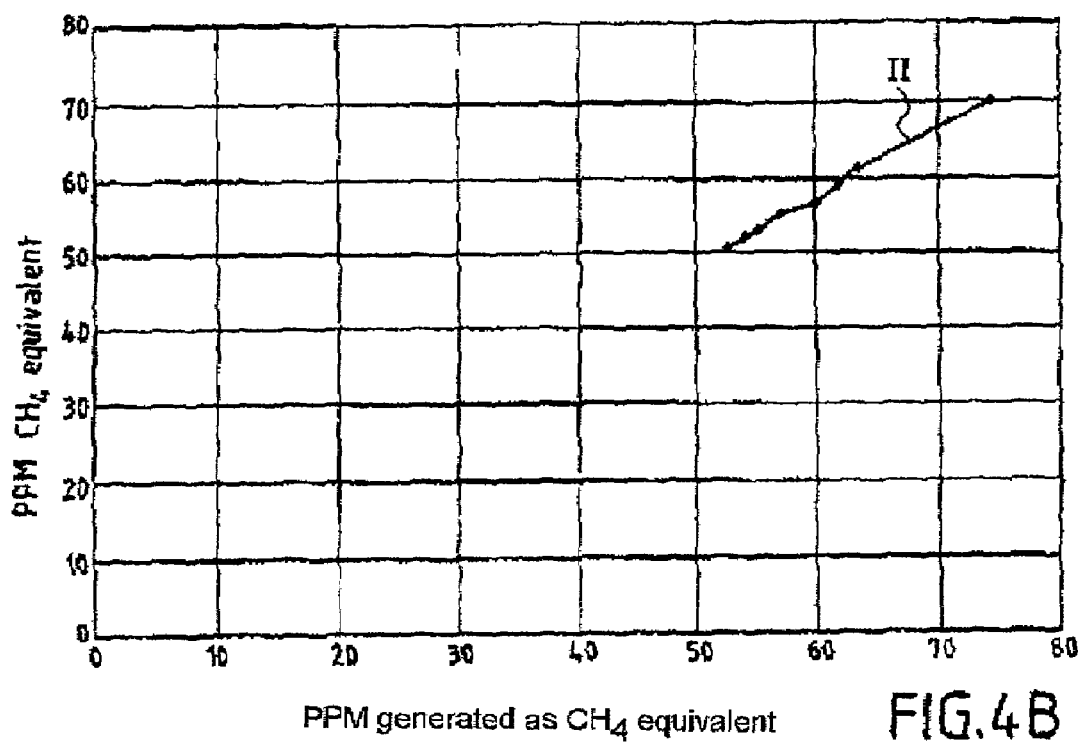

FIGS. 4A and 4B represent the response of the dilution of an HCnM mixture comprising 10.7 ppm of $C_2H_4$ in oxygen possessing 52.9 ppm of $CH_4$ with oxygen possessing 52.7 ppm of $CH_4$ (this makes it possible to gradually dilute the HCnM mixture and thus to vary the concentration of $C_2H_4$ while retaining a constant concentration of $CH_4$). This trial, and in particular curve I, shows that it is possible to estimate an HCnM detection threshold below 5 ppm as $CH_4$ equivalent, i.e. approximately less than 2 to 3 ppm of $C_2H_4$.

Figure 5A:
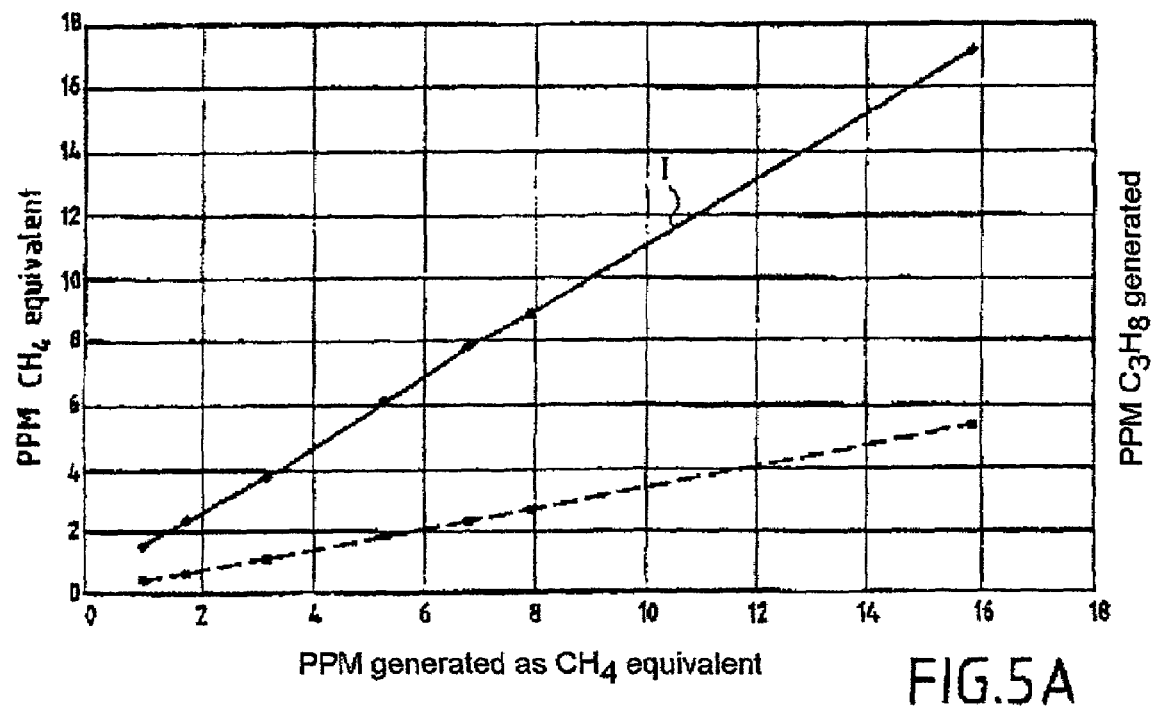
Figure 5B:
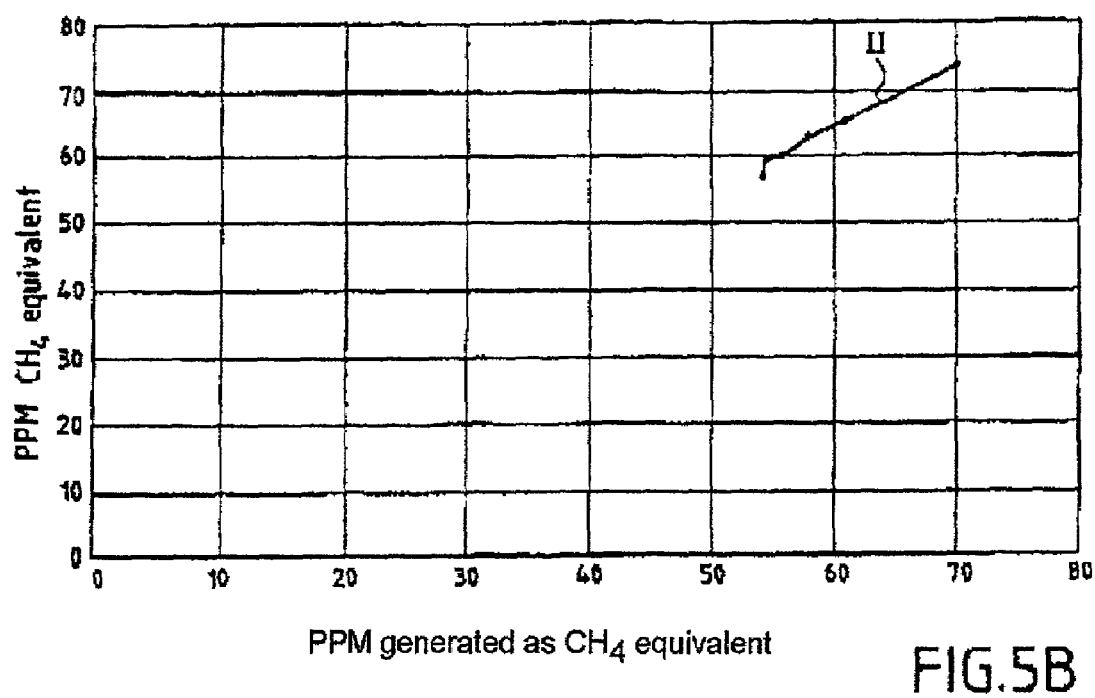

FIGS. 5A and 5B represent the response of the dilution of an HCnM mixture comprising 5.3 ppm $C_3H_8$ in oxygen possessing 49.7 ppm of $CH_4$ with oxygen possessing 52.7 ppm of $CH_4$. This trial shows, as above, an HCnM detection at less than 5 ppm as $CH_4$ equivalent, i.e. less than 2 ppm as $C_3H_8$.

Figure 6A:
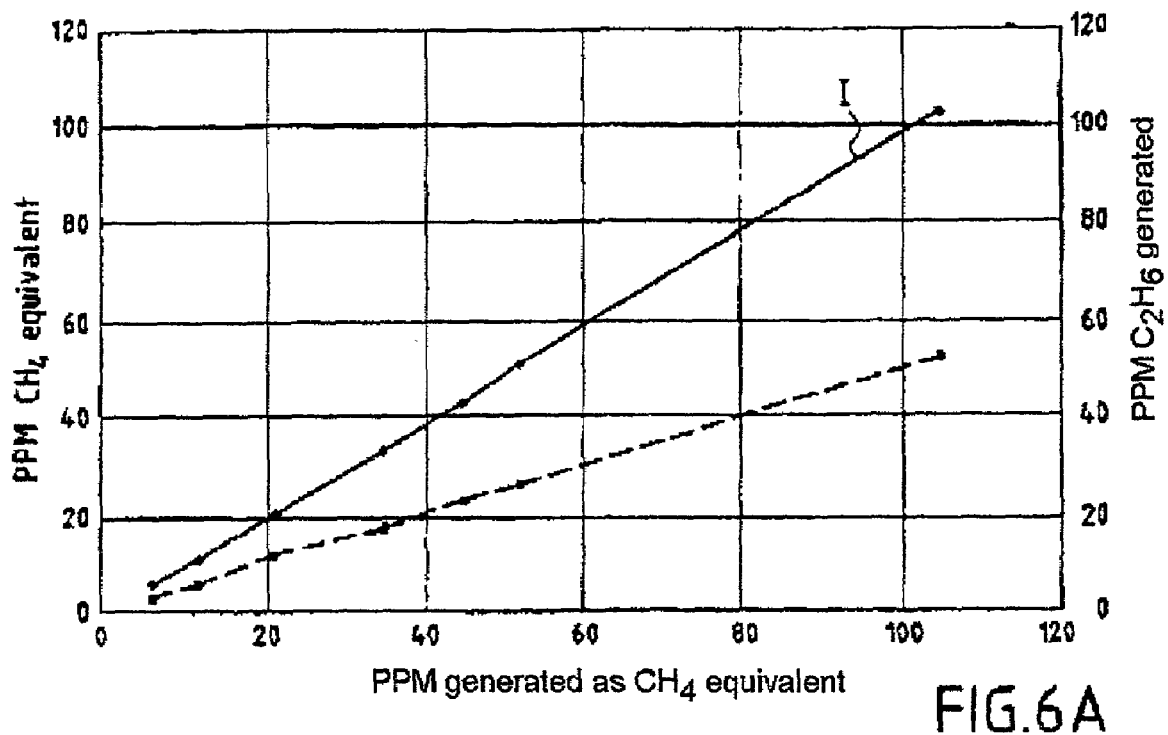
Figure 6B:
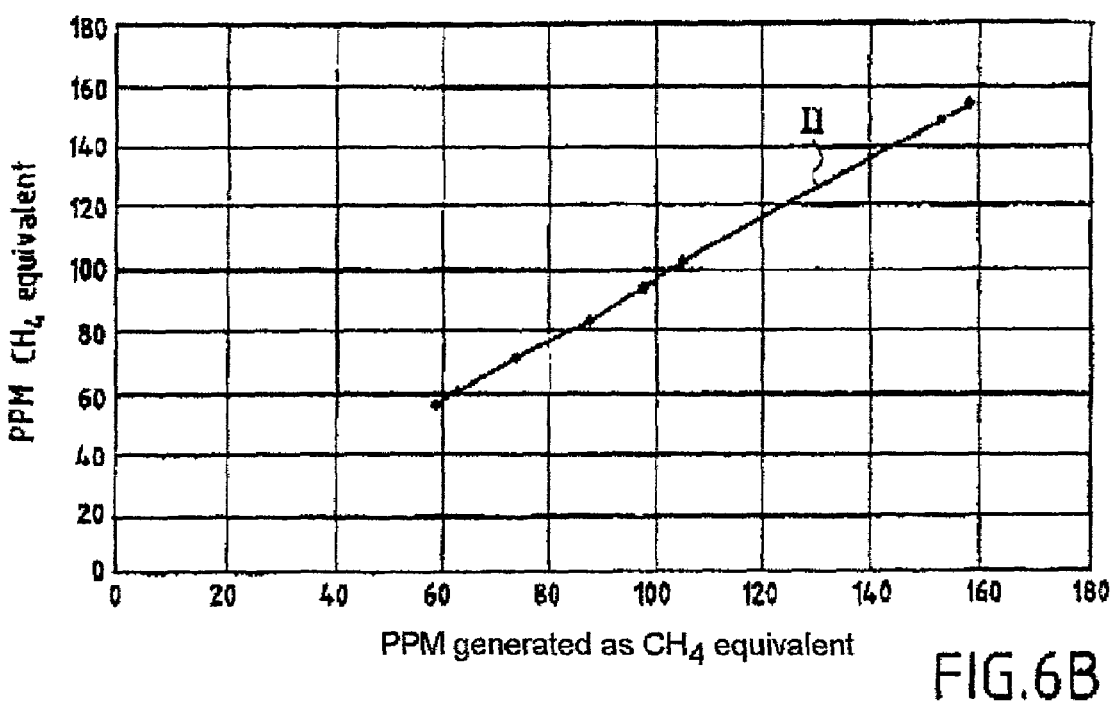

FIGS. 6A and 6B represent the response of the dilution of an HCnM mixture comprising 52.2 ppm of $C_2H_6$ in oxygen possessing 52.5 ppm of $CH_4$ with an $O_2$ mixture possessing 52.7 ppm of $CH_4$. This trial confirms the preceding results and makes it possible to verify the linearity of the response of the device from 0 to 160 ppm as $CH_4$ equivalent.

In the 3 examples given above, curve I shows that it is possible, according to the invention, to detect less than 5 ppm of nonmethane hydrocarbons (as $CH_4$ equivalent), in approximately 50 ppm of methane.

Following these trials, the drift of the device with regard to the measurement carried out on oxygen from the zero circuit (oxygen circulating via route 16 of the diagram in FIG. 2) was measured. Over approximately twenty hours, the HCnM drift is less than 0.1 ppm.

It should be noted that impurities can poison the catalyst when it is used directly on ambient air as gas to be analysed. In contrast, such impurities do not exist when oxygen is used as gas to be analysed, as in the context of the present invention (and in particular oxygen resulting from the unit for the production of gases from the air). The use according to the present invention thus makes it possible to increase the duration of use of the catalysts.

According to one result example, the invention makes it possible to detect less than 5 ppm of hydrocarbons, as methane equivalent, in oxygen comprising approximately 50 ppm of methane (see FIGS. 4A to 6B commented upon above), i.e. less than 2 to 3 ppm of $C_2$ nonmethane hydrocarbons, less than 2 ppm of $C_3$ nonmethane hydrocarbons and less than 1 ppm of $C_4$ nonmethane hydrocarbons.

According to another result example, the invention makes it possible to detect less than 1 ppm, as $CH_4$ equivalent, of HCnM (of $C_2$ and/or $C_3$ and/or $C_4$ type), in particular in oxygen comprising 10 ppm of $CH_4$ (see FIG. 3 and corresponding commentary above), i.e. less than 0.5 ppm of $C_2H_6$, 0.3 ppm of $C_3H_8$ and 0.25 ppm of $C_4H_{10}$.

According to yet another result example, the invention makes it possible to detect less than 5 ppm, as $CH_4$ equivalent, of HCnM ($C_2$ and/or $C_3$), in particular in oxygen comprising 50 ppm of $CH_4$ (see FIGS. 4A–6B commented upon above), i.e. less than 2 to 3 ppm of $C_2$ and less than 2 ppm of $C_3$.

Figure 7:
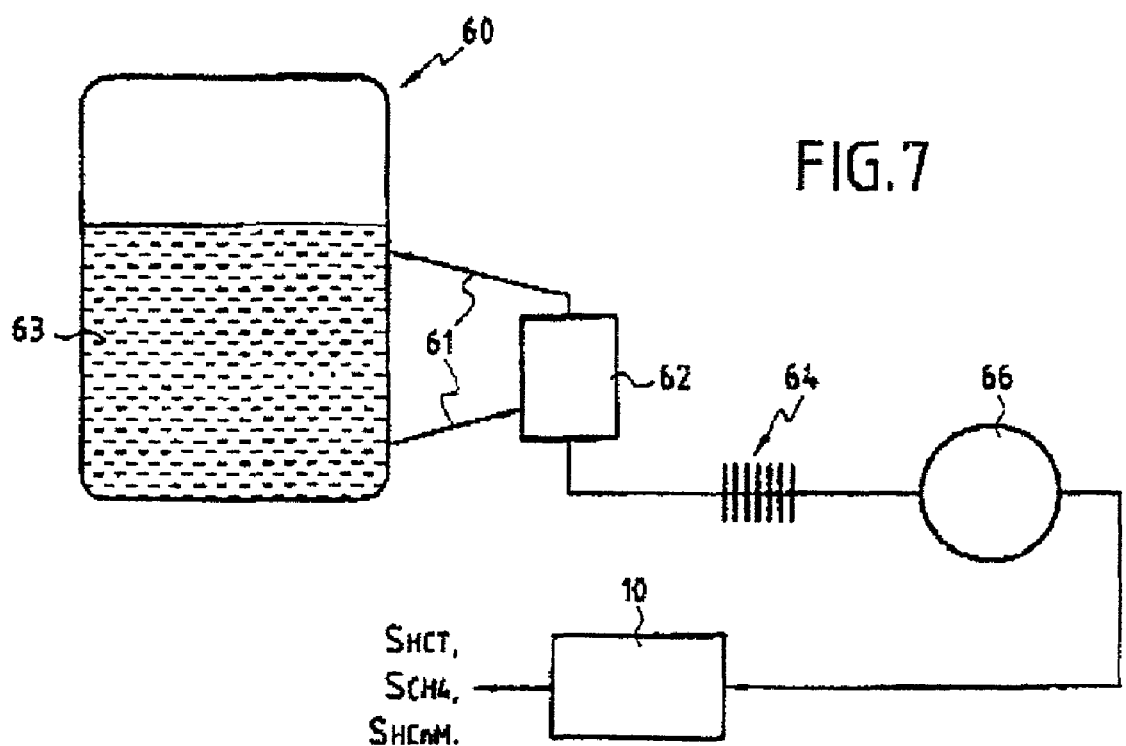
FIGS. 7 and 8 represent a device for the withdrawal of a sample and for analysis from a liquid oxygen bath.
Figure 8:
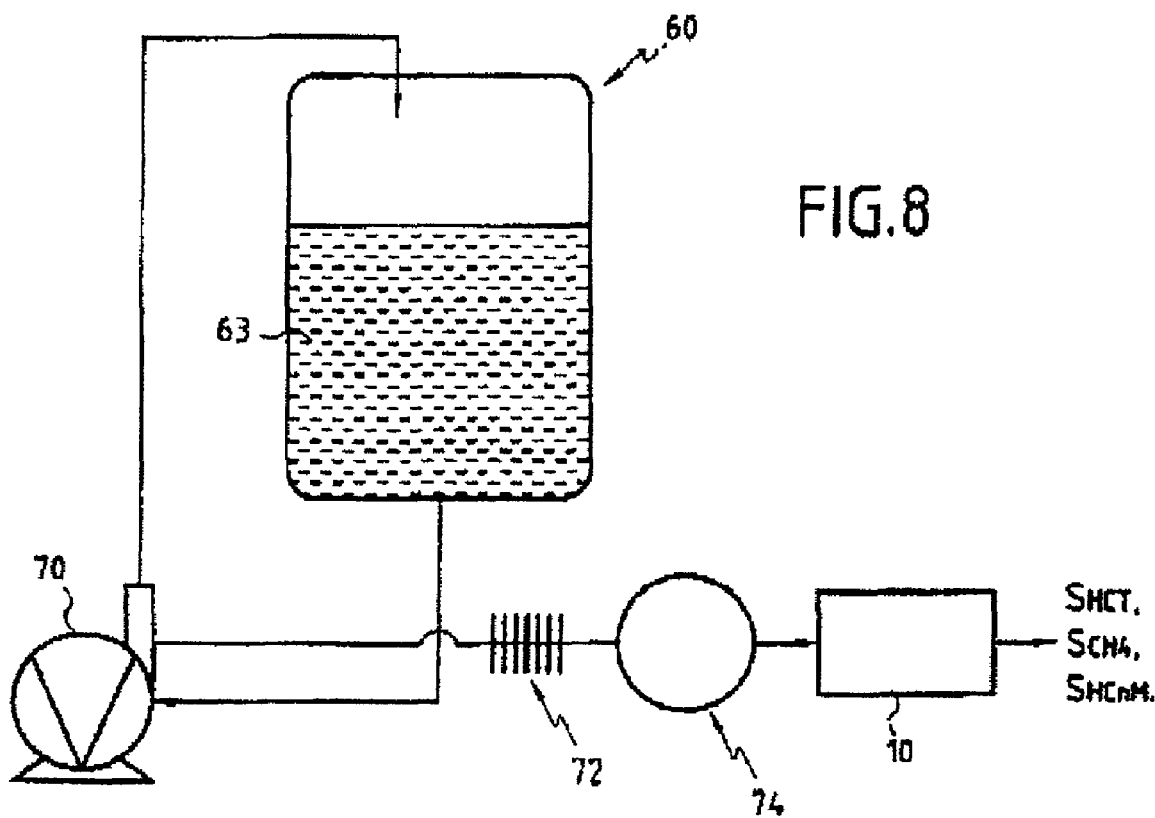

A device and a process as described above can be used in a unit for the production of gases from the air. An example of such a use is illustrated in FIGS. 7 and 8.

In these figures, the reference 60 denotes a liquid oxygen tank comprising a liquid oxygen bath 63. A sample of liquid oxygen is withdrawn from this bath via a pipe of a pump 70 for raising liquid (FIG. 8) or over a sampler 61 of lift type (FIG. 7). This second solution comprises a circulation of liquid towards a small tank 62 situated close to the wall of the tank 60. Complete evaporation of the liquid subsequently takes place in an evaporator composed of a capillary and an atmospheric exchanger 64, 72. The constituents of the gas mixture to be analysed are subsequently homogenized using a mixer 66, 74. The flow rate of the gas sample is, for example, approximately 0.5 to 1 $Sm^3/h$. These two devices make it possible to rapidly sample and convey, to the analyser 10 for hydrocarbons, a gas sample representative of the liquid in the bath 63 of the production unit. They also make it possible to withdraw a liquid which is often replaced: this is because the composition of the liquid present in the tank 60, and in particular the impurities which are to be measured with the device according to the invention, can vary over time. It is thus preferable to have in the withdrawal circuit, at any instant, a sample which represents, in as exact a manner as possible, the composition, at the same instant, of the liquid in the tank 60. This is rendered possible here by the use of means such as the pump 70 for raising liquid or the sampler 61 of lift type.

A system and a process according to the invention, such as, for example, described above in connection with FIG. 1 or 2 or 7 or 8, make it possible to monitor the level of nonmethane hydrocarbons in oxygen and in particular in a liquid oxygen bath, such as the bath of the evaporators of units for the production of gases from the air. When the level or the concentration of nonmethane hydrocarbons exceeds a certain limit value (which, as is understood from FIGS. 3 to 6B, can be of the order of a few ppm, as methane equivalent, for example 5 ppm as methane equivalent or less, for example even 1 ppm as methane equivalent), an alarm can be triggered and a risk of explosion is thus avoided or reduced. The limit values can, for example, be defined in the operating instructions of the production units or can be stored in memory in the processing unit 7 (see FIG. 1) which carries out the measured values-limit values comparison.

In the case of a unit for the production of gases from the air, the continuous measurements of the combined hydrocarbons, of methane and of the nonmethane hydrocarbons make it possible, in the event of exceeding preset concentrations of nonmethane hydrocarbons, to trigger procedures for rendering the production unit safe. For example, depending upon the levels of the alarms, action may be taken with respect to the operation of the purification of the incoming air and/or with respect to the operation of the production and/or shutdown of the production.

The invention claimed is:

1. A process for the detection of hydrocarbons other than methane in a liquid oxygen bath of an evaporator of a unit for the production of gases from the air, comprising the steps of:
    (1) withdrawing a sample of liquid oxygen from the said bath,
    (2) evaporating said liquid oxygen, thereby producing an evaporated gas comprising at least 95% oxygen, and containing methane and hydrocarbons other than methane, and
    (3) detecting the level of hydrocarbons other than methane in the said evaporated gas, said detection comprising the following stages:
        (a) adding hydrogen to said evaporated gas to provide a hydrogen/oxygen ratio between 10% and 40%,
        (b) measuring the level of combined hydrocarbons in said gas, providing a first value for the combined hydrocarbons,
        (c) incinerating the hydrocarbons other than methane in said gas,
        (d) measuring the level of methane in said gas, providing a second value, and
        (e) calculating the amount of hydrocarbons other than methane by the difference between the first value and the second value.

2. The process according to claim 1, wherein said hydrocarbons other than methane are present, with respect to the methane, in a proportion on the order of a few percent.

3. The process according to claim 2, wherein said hydrocarbons other than methane are present, with respect to the methane, in a proportion of less than 6%.

4. The process according to claim 2, wherein said gas comprises less than 50 ppm of methane.

5. The process according to claim 2, wherein said hydrocarbons other than methane are present at a concentration of less than 5 ppm in the oxygen.

6. The process according to claim 3, wherein said hydrocarbons other than methane are present, with respect to the methane, in a proportion of less than 5%.

7. The process according to claim 3, wherein said hydrocarbons other than methane are present, with respect to the methane, in a proportion of less than 4%.

8. The process according to claim 3, wherein said hydrocarbons other than methane are present, with respect to the methane, in a proportion of less than 3%.

9. The process according to claim 1, wherein hydrocarbons other than methane are incinerated using a catalyst.

10. The process according to claim 9, wherein the temperature of the catalyst is such that less than 5% of the methane present in the gas is incinerated.

11. The process according to claim 10, wherein the temperature of the catalyst is between 160° C. and 190° C.

12. The process according to claim 1, wherein the detection is carried out by a flame ionization detector.

13. The process according to claim 12, wherein the temperature of the catalyst is such that less than 5% of the methane present in the gas is incinerated.

14. A process for the detection of hydrocarbons other than methane in a liquid oxygen bath of an evaporator of a unit for the production of gases from the air, comprising:
    withdrawing a sample of liquid oxygen from the said bath,
    evaporating said liquid oxygen, producing an evaporated gas,
    detecting the level of hydrocarbons other than methane in the said evaporated gas, according to claim 12.

15. The process according to claim 1, wherein the withdrawal of the sample is carried out using a pipe of a pump for raising liquid or a sampler of a lift type.

16. The process according to claim 1, additionally comprising a stage of triggering an alarm when the concentration or the level of hydrocarbons other than methane in the said evaporated gas exceeds a certain limit value.

17. The process according to claim 1, said gas comprising at least 99% oxygen.

18. The process according to claim 1, said gas comprising at least 99.5% oxygen.

19. A device for the detection of hydrocarbons other than methane in a liquid oxygen bath of an evaporator of a unit for the manufacture of gases from the air, comprising:
    means for the withdrawal of a sample of liquid oxygen from the said bath, means for the evaporation of said liquid oxygen, producing an evaporated gas,
means for introducing hydrogen into said evaporated gas,
means for the detection of combined hydrocarbons in said gas, providing a first value for combined hydrocarbons,
means for combustion of hydrocarbons other than methane,
means for the detection of methane, providing a second value,
means for calculation of the amount of hydrocarbons other than methane by the difference between the first value and the second value, and
means for triggering an alarm when the concentration or the level of hydrocarbons other than methane in said evaporated gas exceeds a certain limit value.

20. The device according to claim 19, wherein the means for the combustion of the hydrocarbons other than methane comprises a catalyst.

21. A device for the detection of hydrocarbons other than methane in a liquid oxygen bath of an evaporator of a unit for the manufacture of gases from the air, comprising:
means for the withdrawal of a sample of liquid oxygen from the said bath,
means for the evaporation of the said liquid oxygen, producing an evaporated gas, and
a detection device according to claim 20.

22. The device according to claim 19, wherein the means for the detection of the combined hydrocarbons and the means for the detection of methane comprises a flame ionization detector.

23. A device for the detection of hydrocarbons other than methane in a liquid oxygen bath of an evaporator of a unit for the manufacture of gases from the air, comprising:
means for the withdrawal of a sample of liquid oxygen from the said bath,
means for the evaporation of the said liquid oxygen, producing an evaporated gas, and
a detection device according to claim 22.

24. A device for the detection of hydrocarbons other than methane in a liquid oxygen bath of an evaporator of a unit for the manufacture of gases from the air, comprising:
means for the withdrawal of a sample of liquid oxygen from the bath,
means for the evaporation of said liquid oxygen, producing an evaporated gas,
means for introducing hydrogen into said evaporated gas,
means for the detection of combined hydrocarbons in said gas, providing a first value for combined hydrocarbons,
catalyst means for combustion of the hydrocarbons other than methane,
means for the detection of methane, providing a second value,
means for calculation of the amount of hydrocarbons other than methane by the difference between the first value and the second value,
means for triggering an alarm when the concentration or the level of hydrocarbons other than methane in said evaporated gas exceeds a certain limit value, and
wherein the means for the detection of the combined hydrocarbons and the means for the detection of methane comprises a flame ionization detector.

* * * * *